United States Patent [19]

Quang et al.

[11] Patent Number: 5,362,452
[45] Date of Patent: Nov. 8, 1994

[54] REACTOR FOR CARRYING OUT A SUCCESSION OF HETEROGENEOUS CATALYSIS AND THERMAL REACTIONS

[75] Inventors: Dang V. Quang, Neuilly Sur Seine; Charles Cameron, Paris, both of France

[73] Assignee: Institut Francais Du Petrole, Rueil Malmaison, France

[21] Appl. No.: 951,126

[22] Filed: Sep. 25, 1992

[30] Foreign Application Priority Data

Sep. 25, 1991 [FR] France ................... 91 11890

[51] Int. Cl.⁵ .................... B01J 8/06; B01J 10/00
[52] U.S. Cl. .................... 422/192; 422/201; 422/218
[58] Field of Search ........... 422/218, 192, 181, 198, 422/199, 200, 201

[56] References Cited

U.S. PATENT DOCUMENTS

| | | | |
|---|---|---|---|
| 2,363,738 | 11/1944 | Mather et al. | 422/218 |
| 3,167,399 | 1/1965 | Hansen | 422/218 |
| 4,225,562 | 9/1980 | Anderson | 55/387 X |
| 4,976,928 | 12/1990 | Foster et al. | 422/218 |

FOREIGN PATENT DOCUMENTS

| | | |
|---|---|---|
| 1188028 | 9/1959 | France . |
| 2641531 | 7/1990 | France . |
| 2016614 | 10/1971 | Germany . |
| 92181 | 9/1959 | Netherlands . |
| 1140071 | 1/1969 | United Kingdom . |
| 2227249 | 7/1990 | United Kingdom . |

Primary Examiner—Timothy M. McMahon
Assistant Examiner—Robert Carpenter
Attorney, Agent, or Firm—Antonelli, Terry, Stout & Kraus

[57] ABSTRACT

A device for carrying out a succession of heterogeneous catalysis reactions and thermal reactions has an external cylindrical envelope with a longitudinal axis, a coaxial gas permeable casing containing a catalyst located within the envelope, a central manifold, a unit for the injection of a principal reagent into the gas permeable casing, a unit for the injection of reactive components for the catalytic reaction into said casing and an outlet for discharging reaction products from the envelope; an internal diameter of the casing being greater than an external diameter of the central manifold in order to create an annular space therebetween for providing sufficient time for products of a catalytic reaction to remain in order to permit a thermal reaction to develop.

15 Claims, 1 Drawing Sheet

REACTOR FOR CARRYING OUT A SUCCESSION OF HETEROGENEOUS CATALYSIS AND THERMAL REACTIONS

BACKGROUND OF THE INVENTION

The invention concerns a device for carrying out a succession of heterogeneous catalysis reactions and thermal reactions. The device may be more particularly used to carry out the methane oxidising and linking catalytic reaction followed by the thermal dehydrogenation of higher methane alkenes, thereby permitting the production of olefines, in particular, ethylene and propylene and higher homologues, from gaseous mixtures containing principally methane.

As described in prior art, the reactors used to carry out a synthesis in a gaseous phase by heterogeneous catalysis operations, as in the case of the catalytic synthesis of ammonia, methanol or heavy alcohols, comprise an external envelope, generally made in one piece and of substantially cylindrical form, and superimposed catalytic beds arranged over the complete horizontal section of the envelope.

The reactors described in prior art do not permit a succession of heterogeneous catalysis reactions and thermal reactions to be carried out in order to increase the efficiency of the catalysis reaction and obtain additional high value products, these being extremely valuable in the petroleum industry.

SUMMARY OF THE INVENTION

Therefore, this invention proposes a device permitting products to be obtained which have many uses in the petroleum industry in that these products may be used as raw materials for many important product synthesis operations. It is possible to use the device described in this invention in order to obtain, for example, an increase in the production efficiency of ethylene and/or propylene and/or, if necessary, other olefines higher than C3, from the processing of natural gas.

The principal concept of this invention is to create a space between a bed arranged to form a cylindrical casing and a central core used as a manifold, in order to permit thermal reactions, that is, those not controlled by a catalyst, to develop.

Another advantage of the invention is to equip the central core of the reactor with a means to permit a quench stage by the injection of a fluid which limits and stops the reactions occurring in the reactor and/or to recover the heat.

The following description defines a transversal section of the annular space as being that portion of the surface area between the two walls defining the surface area and a transversal section of the casing as being that portion of the surface area between the two edges defining this surface area.

The device, in accordance with the invention, for permitting a succession of heterogeneous catalysis and thermal reactions to be carried out, comprises a substantially external cylindrical envelope having a longitudinal axis and a co-axial casing containing a catalyst located within the envelope, a central manifold, means of injecting a principal reagent into the envelope means of injecting reactive components for the catalytic reaction and a means for discharging the products and is characterised in that the catalyst is arranged in the form of a catalytic bed over the full height of the casing and in that the internal diameter of the casing exceeds the external diameter of the central manifold in order to create a space which permits the products to remain for a sufficient time in order to permit a thermal reaction to occur.

The catalytic bed may comprise a single bed or, if necessary, it may be compartmented.

The casing may comprise two co-axial cylindrical tubes.

An annular space between the casing and the central manifold has a transversal section where the surface area is at least equal to, and preferably not less than, twice the surface area of the transversal section of the casing.

The annular space may be equipped with a means of injection permitting the introduction of reagents.

The means of injection may comprise tubes or perforated hollow panels.

The central manifold or, central core, is defined by a wall or circular section and a layer of insulating material. By using an insulating material, co-existence is possible between the products obtained following the thermal reaction and the cooling means situated in the central manifold, the differences in temperature between the products of reaction and the cooling means of cooling being very important.

The layer of insulating material is fixed to the circular section or the wall of the manifold.

The insulating material may comprise a refractory material, such as brick, cement, silica, glass wool, magnesia or rock or other refractory materials. The refractory material will, preferably, have a low external specific surface area.

The wall of the manifold and the tube of insulating material are provided with orifices where the sections are dimensioned in order that the speed of the reaction effluents passing through each of the said orifices is not less than one meter per second and, preferably, not less than ten meters per second and, again, preferably, not less than fifteen meters per second. All the effluents therefore have a minimum speed through the orifices and therefore the reaction effluents are uniformly distributed when passing over the full height of the reactor, through the orifices.

The central manifold contains, preferably, at least one device permitting a quench stage to be carried out or the recovery of heat.

The casing may be defined by panels positioned radially relative to the axis of the envelope, the said panels being connected together by sealed wall surfaces. In this case, it is possible to use rectangular panels.

The sealed wall surfaces connecting the panels comprise, preferably, cylindrical sections which are co-axial to the envelope, with pyrolysis of its higher homologues, in particular, ethane and propane, into C2+ olefines.

The device described above may, more particularly, be used to carry out the methane oxidising and linking operation.

BRIEF DESCRIPTION OF THE DRAWINGS

Other characteristics and advantages of this invention will become more apparent on reading the following description and by referring to the accompanying Figures which show two possible reactor structures, permitting a succession of heterogeneous catalysis operations and thermal reactions to be carried out, these examples obviously being not limiting, wherein.

DETAILED DESCRIPTION OF THE INVENTION

The device in accordance with the invention permits, in particular, successive heterogeneous catalysis and thermal reactions to be carried out, such as those described in the published application for French patent FR-2,641,531 and U.S. Pat. No. 5,025,108.

The reactor to be described in the following text permits the mixing of a principal reagent, such as, natural gas, with those reagents necessary for a catalytic reaction, before permitting them to enter the catalytic bed where the catalysis reaction is to take place. One part of the products obtained and the new reagents introduced into the reaction space will react thermally by using part of the heat released during the preceding catalysis operation and therefore permitting the temperature of the gas to be lowered.

Figure 1:
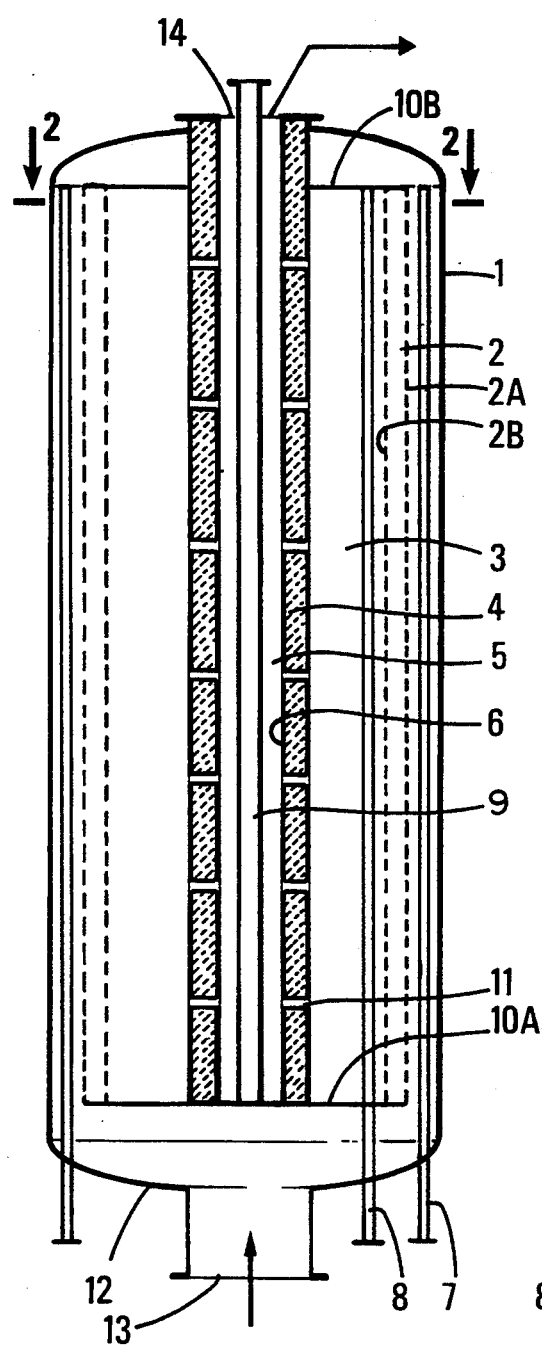
FIG. 1 represents a preferred embodiment of a cylindrical reactor in accordance with the invention.

The reactor shown in FIG. 1 comprises an envelope 1, substantially cylindrical and thermally insulated, in which is arranged a co-axial tubular cylindrical casing 2.

This casing 2 comprises two co-axial tubes, the walls 2A, 2B being permeable to the gas and to the reagents involved during the catalysis reaction.

In the annular space between the walls 2A, 2B, a catalyst is introduced to form a single fixed bed or, if necessary, with compartments, this bed being permeable to the gases and the reagents.

The catalyst comprises one of the forms normally used in this type of reaction, for example, in the form of granules, extruded sections, spheres, etc.

An annular space 3 is provided between the wall 2B of the casing 2 and a tube 4 made from an insulating material and inside which passes a manifold 5 comprising a tube or circular section 6.

By using a means of injection, such as one or several tubes 7 pierced with orifices and external to the casing 2, for example, it is possible to inject those reactive components which are essential for initiating and maintaining the heterogeneous catalysis reactions carried out.

Another means of injection, such as one or several tubes 8 pierced with orifices, for example, permits the injection of other reactive agents which are also used for the reaction taking place and which will be described later in the description. A means of cooling, such as one or several tubes 9, may be positioned in the manifold 5 to permit the passage of a cooling fluid (liquid known as the "quench") or to permit the recovery of heat.

A first end wall 10A closes the lower end of the casing 2, the central manifold 5 and the annular space 3. Another sealed wall surface 10B at the other end of the envelope 1 closes the casing 2 and the annular space 3. The central manifold 5 passes through this.

Orifices 11 in the wall 6 and the layer of insulating material provide a communication between the annular space 3 and the manifold 5 in order to permit the passage of the reaction effluents present in the space 3 and, in particular, the products obtained during the thermal reactions.

The envelope 1 is closed at each of its ends by an end plate 12 which is, preferably, of ellipsoidal form.

An opening 13 is provided in the lower part of the envelope 1 and forms a communication between the space for the envelope external to the casing 2 with the means of injection for the principal reagent. This reagent, mixed with another suitable reagent for the catalytic reaction, such as a gas containing molecular oxygen, for example, passes through the catalytic bed of the casing 2 where the catalytic reaction will take place.

The envelope 1 comprises, at its upper end, an orifice 14 permitting the effluents present in the manifold 5 to be removed.

The casing containing the catalytic bed is the point where the heterogeneous catalysis reaction occurs, for example, in the case of the methane oxidising and linking stage between the natural gas or, more particularly, the methane and a reagent introduced, at the final stage, by the means of injection 7. In the case of the methane oxidising and linking reaction, the reagent injected by the means 7 is a gas containing molecular oxygen, for example, oxygen or air.

A reduced thickness of the catalytic bed contained in the casing permits a reduction in the pressure drop when the gases and the reagents are passing through the catalytic bed. For this reason, a thickness for the catalytic bed is chosen, this preferably not exceeding 50 cm and, again preferably, not exceeding 30 cm.

The area of the transversal section of the annular space 3 (FIG. 2) is at least equal to the area of the transversal section of the casing 2. Preferably, the value of the area for the transversal section of the space 3 is not less than twice the transversal section of the casing 2, in order to ensure that the products remain a sufficient time to permit at least, in part, a thermal conversion of the products obtained during the first heterogeneous catalysis reaction stage and the new reactive components inherent in the thermal reactions introduced using the means of injection 8.

Therefore, in order to process products obtained during the heterogeneous catalysis reaction, such as ethane and, if necessary, and the hydrocarbons injected by the means of injection 8, a pyrolysis stage is carried out on the mixture resulting from the two gaseous flows. This operation improves the efficiency of the methane oxidising and linking operation, by increasing the proportion of olefines, these products being considerably more useful as they are used as a base for the production of petrochemical products.

Figure 2:
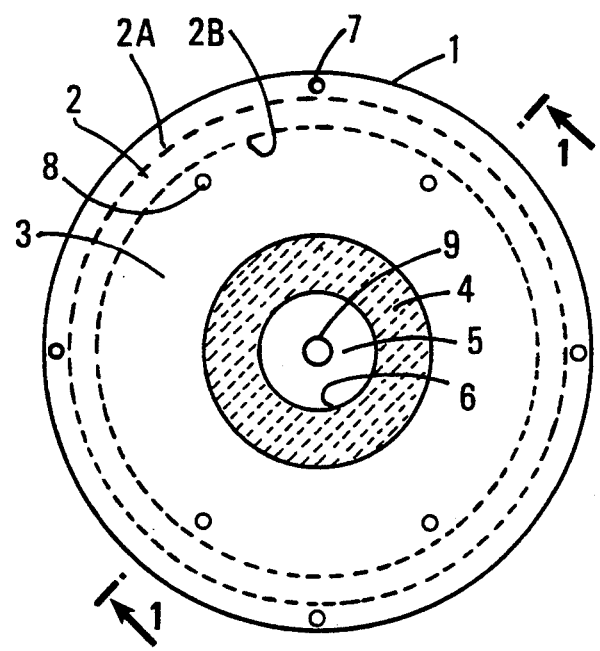
FIG. 2 shows a transversal section of the reactor represented in FIG. 1.

In the example represented in FIG. 2, the material for the tube 4 is fixed to the side of the wall 6, situated on the side of the thermal reaction space 3. Another possibility is to fix this material against the wall 6, internally, on the side of the manifold 5, so that it is then no longer in direct contact with the products and reactions which take place in the space 3.

The material of the tube 4, preferably comprises a refractory material which is a low conductor of heat. For example, it is possible to chose, as the material, brick, cement, silica, glass wool, magnesia or rock or other refractory materials. By using this arrangement, co-existence is possible between the products present in the thermal reaction zone 3 and the means of cooling or quenching, passing into the central manifold 5, by thermally insulating the space where the thermal reactions occur, and the central core of the manifold.

The tube 4 surrounding the wall 6 of the central manifold 5 will be, preferably, of circumferential form.

The means of injection 7 permits, as already described, the introduction of the reactive components involved during the heterogeneous catalysis reaction inside the casing 2 and in the presence of the catalytic bed and where mixing with the principal reagent occurs as the final stage inside the envelope 1 itself. The lower end of the tube 7 comprising the means of injection emerges, for example, outside the envelope 1 and its upper end is closed at the height of the sealed wall surface 10B situated at the upper end of the casing. It is possible to provide several tubes 7 positioned around the casing 2 containing the catalytic bed. In the case of methane oxidisation, the reactive component introduced by the tube 7 may be oxygen at a high temperature, mixed with nitrogen or steam. Mixing takes place as the final stage, in order to minimise the spontaneous reaction which occurs between the oxygen and the methane.

The means of injection 8 introduces new reactive components which, by reacting thermally in the annular space 3, reduce the temperature existing in that space. The thermal reaction may comprise, for example, thermal cracking of the ethane into ethylene or by cracking a cut of hydrocarbons, for example, naphtha, into C2+ olefines.

The means of injection 7 and 8 comprise, preferably, tubes or, again, perforated panels, closed at one of their ends. The orifices of these tubes or panels 7 and 8 will be orientated, for example, so as to direct the jets of gas ejected parallel to the tangent for the casing containing the catalyst. This orientation is preferential but does not limit the scope of the invention. It is possible to adopt some other orientation for the orifices in order to permit the products injected to react, as efficiently as possible, with the reactive products present in the annular space 3.

The means of cooling 9 for the central manifold 5 may comprise, for example, tubes with orifices for the injection of liquid, known as the "quench" or direct cooling stage. Another method of construction uses thermal exchange tubes producing, for example, steam under pressure.

The overall area of the orifices 11 is chosen so that the reaction effluents passing through the orifices have a speed of not less than one meter, preferably not less than ten meters per second and, again preferably, not less than fifteen meters per second. The value for this speed is obtained by dividing the total flow of all the effluents, expressed in cubic meters per second, by the section representing all the sections of all the orifices. Optimisation of the ratio between the overall area of the orifices 11 and the total surface area of the central manifold 5 permits a high rate of circulation for the products and therefore achieves uniform and sufficiently rapid discharge of the products obtained following the thermal cracking stage. It is possible to ensure that the same quantity of reaction effluents is discharged by the lower orifices and by the upper orifices of the central core.

Figure 3:
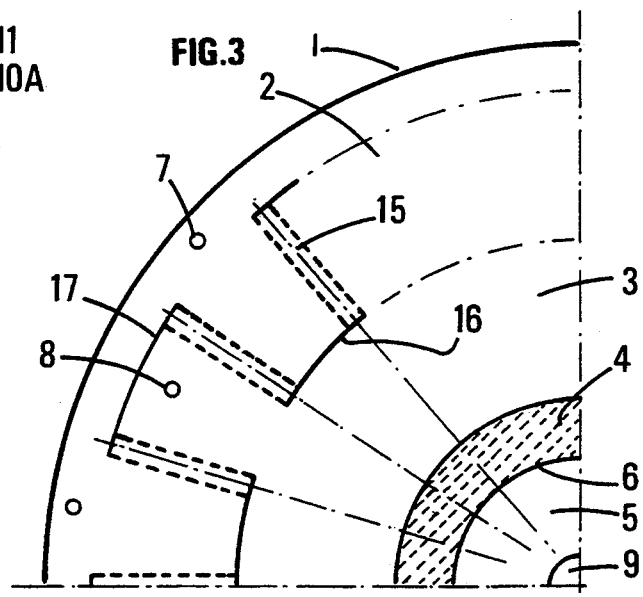
FIG. 3 represents another variant in the case of a reactor comprising a catalytic bed constructed from radial panels.

The method of construction shown in FIG. 3 differs from that shown in FIGS. 1 and 2 in that the catalytic bed is arranged in a casing 2 in the form of crenellations and comprising rectangular panels 15 filled with a catalyst of granular type, for example, and connected together by sealed wall surfaces 16, 17. These form, for example, sections of cylinders which are coaxial to the envelope 1.

By connecting the parts 16, 17 and the panels 15 containing the catalytic bed, a continuous wall surface is defined which limits the space for the thermal cracking operation 3.

The orifices of the injection tube 8, or each of these, are arranged so that the jets of gas have, preferably, an orientation parallel to a radial direction, for a panel 15 comprising the casing 2. Any other orientation permitting the reactions to take place may, however, be adopted.

The device, as described above, permits successive thermal reactions and heterogeneous catalysis reactions to be carried out, such as those described in the above patent application FR-2,641,531 and U.S. Pat. No. 5,025,108. Obviously, it may be applied to any reaction requiring this type of structure for the device.

A preferential process carried out in the device described above may comprise the following stages: the principal reagent is introduced, such as natural gas treated beforehand so that it substantially only contains methane, preferably in the presence of an inert gas such as steam in the case of the methane oxidising and linking operation, using the means of introduction 13 situated at the lower end of the envelope 1. This reagent mixes with the reactive products introduced by the tube 7 before entering the catalytic bed contained in the casing 2, in the form of a mixture of the two products. The reactive products may comprise, for example, oxygen at a high temperature which will react with the methane. The oxygen may, if necessary, be diluted with the nitrogen or the steam. The heterogeneous catalysis reaction occurs when in contact with the catalytic bed in the casing 2. The products obtained during this reaction then pass into the thermal reaction space 3, where they are mixed with the new reagents introduced by the means of injection 8, this permitting the temperature of the gas to be reduced by an endothermic cracking reaction. The heat released during the heterogeneous catalysis reaction is partially used to convert the reagents introduced by the tubes 8 into C2+ olefines.

The products resulting from the thermal reactions then pass into the manifold 5 before leaving by the orifice 14. The reactions are stopped by the cooling or quench fluid circulating, preferably, in the central manifold. Therefore, for the purpose of the methane oxidising and linking stage, it is possible to introduce, as a new product, ethane, a cut of C2+ and/or a cut of hydrocarbons, such as a cut of naphtha, in order to partially absorb the heat released during the exothermic catalysis reaction stage and to increase the olefines content, such as, ethylene, propylene, or those olefines higher than C3, by means of thermal reactions. In this way, it is possible to produce a greater quantity of olefines relative to the quantity normally obtained during a heterogeneous catalysis reaction only, not followed by a thermal reaction stage.

Obviously, various modifications and/or additions may be made to the process and to the device, the description being given as an illustration only and being in no way limiting, without exceeding the scope of the invention.

We claim:

1. A device for carrying out a succession or heterogeneous catalysis and thermal reactions, which comprises an external substantially cylindrical envelope having a longitudinal axis, a co-axial, gas-permeable casing arranged within said envelope, said casing having an internal diameter and an external diameter and containing a catalyst, a central manifold, means for injecting a principal reagent into said gas permeable casing, means for injecting reactive components for a catalytic reaction into said gas permeable casing and means for discharging reaction products from the manifold, wherein the catalyst is arranged in the form of a catalytic bed over a full height of the casing and the internal diameter of the casing exceeds an external diameter of the central manifold in order to create an annular space which permits products of the catalytic reaction to remain for a sufficient time in order to permit a thermal reaction to occur; the central manifold being defined by a wall and a tube of insulating material, said tube being supported and in contact with the wall.

2. A device according to claim 1, wherein the catalytic bed comprises a single continuous bed.

3. A device according to claim 1, wherein the catalytic bed comprises a plurality of discreet compartments within said casing.

4. A device according to claim 1, wherein the casing comprises two co-axial cylindrical gas permeable tubes.

5. A device according to claim 1, wherein a transversal section of the annular space between the casing and the central manifold has a surface area which is at least equal to twice a surface area of a transversal section of the casing.

6. A device according to claim 1, wherein a transversal section of the annular space between the casing and the central manifold has a surface area which is not less than twice a surface area of the transversal section of the casing.

7. A device according to claim 1, wherein the annular space is provided with injection means for introducing reagents into said annular space.

8. A device according to claim 7, wherein the injection means comprises at least one perforated tube or perforated hollow panel.

9. A device according to claim 1, wherein the tube of insulating material in contact with the wall comprises a refractory material.

10. A device according to claim 1, wherein the wall of the central manifold and the tube of insulating material have orifices aligned with each other, cross sections of the orifices being such that reaction effluents passing through said orifices have a speed of not less than 1 meter per second.

11. A device according to claim 1, wherein at least one heat exchange means for cooling or for recovery of heat is positioned within the central manifold.

12. A device according to claim 1, wherein the casing comprises a plurality of gas permeable panels positioned radially relative to the longitudinal axis of the envelope, said panels being spaced from each other and being connected together by sealed wall surfaces.

13. A device according to claim 12, wherein the panels are rectangular in cross section.

14. A device according to claim 13, wherein the sealed wall surfaces connecting the panels comprise cylindrical sections which are co-axial with the longitudinal axis of the envelope.

15. A device for carrying out a succession or heterogeneous catalysis and thermal reactions, which comprises an external substantially cylindrical envelope having a longitudinal axis, a co-axial, gas-permeable casing arranged within said envelope, said casing having an internal diameter and an external diameter and containing a catalyst, a central manifold, means for injecting a principal reagent into said gas permeable casing, means for injecting reactive components for a catalytic reaction into said gas permeable casing and means for discharging reaction products from the manifold, wherein the catalyst is arranged in the form of a catalytic bed over a full height of the casing and the internal diameter of the casing exceeds an external diameter of the central manifold in order to create an annular space which permits products of the catalytic reaction to remain for a sufficient time in order to permit a thermal reaction to occur; said cylindrical envelope being provided with a first end wall closing a lower end of the casing, an end of the central manifold, and the annular space; and another end wall closing a top end of the casing and the annular space, said central manifold extending through said another end wall.

* * * * *